US009039969B2

(12) United States Patent
Tustison et al.

(10) Patent No.: US 9,039,969 B2
(45) Date of Patent: May 26, 2015

(54) ELECTROSPUN FIBER PRE-CONCENTRATOR

(75) Inventors: Randal W. Tustison, Andover, MA (US); Vincent B. Tucci, Jr., Littleton, MA (US); Jiyun Imholt, Methuen, MA (US); Mary Herndon, Littleton, MA (US)

(73) Assignee: RAYTHEON COMPANY, Dallas, TX (US)

( * ) Notice: Subject to any disclaimer, the term of this patent is extended or adjusted under 35 U.S.C. 154(b) by 552 days.

(21) Appl. No.: 12/578,941

(22) Filed: Oct. 14, 2009

(65) Prior Publication Data

US 2011/0086415 A1    Apr. 14, 2011

(51) Int. Cl.
*D01F 1/09*    (2006.01)
*G01N 1/40*    (2006.01)
*D01F 1/10*    (2006.01)

(52) U.S. Cl.
CPC .. *D01F 1/09* (2013.01); *G01N 1/40* (2013.01); *B01D 2239/025* (2013.01); *B01D 2239/04* (2013.01); *B01D 2239/0631* (2013.01); *D01F 1/10* (2013.01)

(58) Field of Classification Search
CPC ............... D01F 1/09; D01F 1/10; G01N 1/40
See application file for complete search history.

(56) References Cited

U.S. PATENT DOCUMENTS

| | | | |
|---|---|---|---|
| 1,975,504 A | 10/1934 | Formhals | 18/8 |
| 4,895,809 A * | 1/1990 | Schlabach et al. | 436/518 |
| 6,753,454 B1 * | 6/2004 | Smith et al. | 602/41 |
| 2004/0005582 A1 * | 1/2004 | Shipwash | 435/6 |
| 2004/0030377 A1 * | 2/2004 | Dubson et al. | 623/1.13 |
| 2004/0076681 A1 * | 4/2004 | Dennis et al. | 424/489 |
| 2006/0148066 A1 | 7/2006 | Senecal et al. | 435/287.2 |
| 2008/0110342 A1 | 5/2008 | Ensor et al. | 96/54 |
| 2008/0150556 A1 | 6/2008 | Han et al. | 324/693 |
| 2008/0184884 A1 | 8/2008 | Jadhav | 95/134 |
| 2008/0236251 A1 | 10/2008 | Tepper et al. | 73/31.05 |

OTHER PUBLICATIONS

International Search Report and Written Opinion; PCT/US2010/051041; pp. 11, Nov. 18, 2010.
Ji et al.; "Gas Sensing Properties of a Composite Composed of Electrospun Poly ( methyl methacrylate ) Nanofibers and in Situ Polymerized Polyaniline"; Sensors and Actuators B 133; pp. 644-649, 2008.

* cited by examiner

*Primary Examiner* — Melanie Y Brown (57) ABSTRACT

The present disclosure relates, in some embodiments, to pre-concentrator compositions, devices, systems, and/or methods for concentrating small quantities of chemical or biological compounds, e.g., CBRNE compounds. A pre-concentrator of the disclosure may be operable to releasably bind and concentrate CBRNE compounds. In some embodiments, a pre-concentrator may comprise a 3-D structure of electrospun nanofibers, that comprise at least one polymer, one conducting agent and at least one chemical-specific functional group and/or biological-specific moiety configured to selectively bind to a CBRNE compound. Bound compounds may be released and detected. Pre-concentrator devices and systems operable to bind, concentrate, and/or detect one or more CBRNE compounds are described. Devices and systems of the disclosure may be configured to concentrate and detect multiple compounds. Methods for synthesizing pre-concentrators as well as methods for concentrating, detecting and identifying compounds of interest are also set forth.

23 Claims, 6 Drawing Sheets

In-line with
HVAC unit 62
70

Fan    Detector → 92

→ 82

Power Source for
Analyte Release

FIGURE 4C

ELECTROSPUN FIBER PRE-CONCENTRATOR

FIELD OF THE DISCLOSURE

The present disclosure relates, in some embodiments, to compositions, devices, systems, and/or methods for sensing, concentrating, detecting and identifying chemical and biological compounds of interest. For example, some embodiments relate to electrospun fiber based pre-concentrator compositions and to devices and systems incorporating the electrospun fiber pre-concentrators which are operable to releasably bind, concentrate, release and detect compounds of interest, especially when present in small concentrations. Methods for using the compositions, devices and systems of the disclosure to detect compounds of interest are also set forth.

BACKGROUND OF THE DISCLOSURE

Chemical sensors, used for detection of variety of chemicals, such as chemical warfare agents, explosive agents and/or pollutants, especially when present as vapors, typically utilize spectrometry systems (such as mass spectrometry (MS)), and/or gas chromatography (GC), as well as electrochemical systems such as surface acoustic wave sensors (SAWS), mass sensors and optical sensors. The need for multiple sensor technologies is driven by the fact that there are a variety of chemical compounds/agents of interest that may need to be detected simultaneously and a variety of desired monitoring conditions and environments in which such chemicals may be found. This issue is further complicated by findings of a recent DARPA study of chemical and biological sensor standards that indicates that the minimal detectable concentration range of interest for chemical/biological agents of primary concern vary by more than $10^6$.

Many of the chemical agents of interest, such as explosive agents, have a very low vapor pressure, for example, as low as 0.1-1.0 millitorr, which makes it difficult to detect such agents, except when present in large concentrations. Thus, sensitivity is a key consideration in chemical sensor development. Regardless of the sensor type, pre-concentrators may be used to control the input airflow to a detector so that the concentration of an agent/compound of interest is optimized for the detection sensitivity.

Typical pre-concentrators for vapor sensing systems rely on collection of the gas in a stainless steel canister or adsorption of the compound/agent (analyte) to be analyzed on a filter. The analyte is typically concentrated using cryogenic techniques (cooling) or pressurization (in the case of the canister method), or with the use of heat or a solvent (in the case of the filter method). These methods rely on long collection time and significant external infrastructure to activate and/or release the compound of interest (analyte).

Furthermore, complicated contact requirements between a pre-concentrator and the external activation and/or release mechanisms are generally required. For example, pre-concentrator units containing electrospun fiber sorbents typically depend on contact with an external heater for heating. These pre-concentrators are limited by uneven heating (due to the contact requirements) which causes gradual or partial release of analytes of interest that may be bound to the pre-concentrator, resulting in inefficient design, sensing and detecting abilities.

On the other hand, use of electrospun fibers for chemical detection has been limited to use of the fiber itself as the detection mechanism. For example, changes to an electrospun fiber's optical fluorescence, resistivity or impedance have been monitored to determine whether an analyte has bound to an electrospun fiber. While such systems may be sensitive and may have a fast response time, they are prone to high rates of false positives and are hampered by limited specificity of detection. Changes in fiber properties are a result of binding rather than binding by a specific analyte. Thus, binding of agents that may not be analytes of interest may also be detected by electrospun fiber based chemical detection systems.

SUMMARY OF THE DISCLOSURE

Accordingly, a need has arisen for improved compositions, devices, systems, and/or methods for sensing and concentrating a variety of compounds/agents of interest, especially when present in small or trace quantities which may then be subject to detecting.

The present disclosure relates, according to some embodiments, to compositions, devices, systems and methods that comprise or use 3-D structures of electrospun nano-fibers having at least one conducting agent and one or more chemo-selective functional groups and/or bio-specific moieties that are operable to bind, concentrate, and release, a variety of compounds/agents of interest, such as but not limited to chemical, biological, radioactive, nuclear and explosive agents (i.e., CBRNE agents), and combinations thereof that may be present at low vapor pressures and/or in small or trace quantities.

In some embodiments, the present disclosure describes a pre-concentrator operable to releasably bind and concentrate one or more compounds of interest, comprising a 3-D nanofiber structure of electrospun fibers, the electrospun fibers comprising at least one polymer, at least one chemo-specific functional group and/or a bio-specific moiety and at least one conducting agent. A chemo-specific functional group may be any chemical functional group configured to selectively bind to the one or more compounds of interest. A bio-specific moiety may be any biological compound, biological molecule, and/or chemical compound, that can selectively bind to one or more biological compounds of interest.

Pre-concentrators of the disclosure may be further operable to release one or more compounds or agents of interest that may be bound and concentrated. Accordingly, chemo-specific functional groups and/or bio-specific moieties of a pre-concentrator of the disclosure may have different respective binding and respective release properties for different compounds of interest. To be operable for release, a chemical functional group or bio-specific moiety comprised in an electrospun fiber of the disclosure may be configured to selectively bind (at respective binding conditions) to the one or more compounds by weak or non-covalent mechanisms such as adsorption, hydrogen bonding, or a weak attractions such as dipole-dipole interactions. In some embodiments, one or more compounds bound to an electrospun fiber pre-concentrator of the disclosure may be released by respective releasing conditions that may dissociate the weak, non-covalent bonds and may include selective desorption, resistive heating of the electrospun fibers, nanoscale Joule-heating effects and/or combinations thereof.

A 3-D nano-fiber pre-concentrator of the disclosure may comprise one or more conducting agents. A conducting agent may confer an intrinsic heating property on a 3-D nanofiber pre-concentrator of the disclosure. In some embodiments, a 3-D nanofiber structure of the disclosure may be an intrinsic heater. In some embodiments, the intrinsic heating may be resistive heating. In some embodiments, 3-D nano-fiber structures of the disclosure may be semiconducting and may be composed of semiconducting nano-fibers. Ability to conduct heat and/or resistive heating of a pre-concentrator may allow for release of bound and concentrated compounds of interest.

This summary contains only a limited number of examples of various embodiments and features of the present disclosure. For a better understanding of the disclosure and its advantages, reference may be made to the description of exemplary embodiments that follows.

BRIEF DESCRIPTION OF THE DRAWINGS

Some embodiments of the disclosure may be understood by referring, in part, to the present disclosure and the accompanying drawings, wherein:

FIGS. 1A, 1B and 1C illustrate examples of pre-concentrators having various 3-D structures, wherein.

FIGS. 3A, 3B and 3C illustrate an example schematic of an electrospun nanofiber fiber design wherein: FIGS. 4A, 4B and 4C illustrate schematics of pre-concentrator devices and systems, wherein

DETAILED DESCRIPTION

Embodiments of the disclosure and its advantages may be best understood by reference to FIGS. 1A-4C wherein like numbers refer to same and like parts.

A pre-concentrator, a device comprising a pre-concentrator, or a system comprising a pre-concentrator, according to the disclosure, may be useful to detect a variety of compounds, such as CBRNE agents. Some non-limiting examples of compounds/agents that may be bound, concentrated and detected by the compositions, devices, systems and/or methods of the disclosure include: chemical warfare agents, chemicals contained in explosives, pollutants, industrial pollutants, toxic industrial wastes, toxic gases, toxic compounds, and biological agents including biological warfare agents, especially when present in small or trace quantities or when present at very low vapor pressures. Such compounds or traces thereof may be generally present dispersed in the air, water and/or in the environment.

The present disclosure relates, in some embodiments, to pre-concentrators comprising 3-D structures of electrospun nano-fibers that have high surface-to-area ratios and comprise 1) at least one polymer; 2) at least one conducting agent; and 3) one or more chemo-selective functional groups or one or more bio-specific moieties which enable a pre-concentrator to bind to and concentrate chemical and/or biological compounds of interest under respective binding conditions. Pre-concentrators of the disclosure may also be operable to release bound compounds of interest under respective releasing conditions. Release of one or more bound compounds of interest may be achieved by changing the respective binding conditions to respective releasing conditions such as by increasing temperature, increasing heat and/or by competitive adsorption with compounds that may have a higher affinity for the chemo-selective functional groups or to the bio-specific moieties of a pre-concentrator.

A conducting agent comprised in a pre-concentrator of the disclosure may allow uniform heating, substantially uniform heating, and/or rapid heating of a pre-concentrator nanofiber by passage of an electric current or by radiant heating. Any electrical energy source such as but not limited to an AC power source or any radiant energy source such as but not limited to lasers or ultraviolet radiations may be used to heat a pre-concentrator of the disclosure to obtain respective releasing conditions. AC power source may be connected directly to the pre-concentrator structure. Radiant energy sources may be used externally by for example shining a laser beam or an ultraviolet light onto a pre-concentrator.

In some embodiments, a dopant may be used as a conducting agent in a pre-concentrator of the disclosure. Dopants may confer semiconducting properties on a pre-concentrator of the disclosure. In some embodiments, a metal may be used as a conducting agent in a pre-concentrator of the disclosure. In some embodiments, both dopants and metals may be used. A dopant or a metal may enable uniform or substantially uniform nano-scale heating and/or cooling of the electrospun fibers of the pre-concentrator. Heating electrospun fibers may be useful for generating respective release conditions for release of one or more bound and/or concentrated compound(s) of interest. While not wishing to be bound by theory, heating may cause respective releasing conditions by providing nano-scale heat energy for dissociation of weak, non-covalent bonds by which compounds of interest may be bound to a pre-concentrator. For example, nano-scale joule heating of the pre-concentrator nano-fibers may dissociate hydrogen bonded compounds of interest from the pre-concentrator fiber. Released compounds of interest may then be made available for analysis by one or more detectors.

3-D Pre-Concentrators

A pre-concentrator of the disclosure comprises electrospun nano-fibers that may be configured to have a 3-dimensional (3-D) structure or design. The 3-D structure of nano-fibers provides a higher medium-to-surface contact area and a better chance and rate of analyte capture and concentration.

Figure 1A:
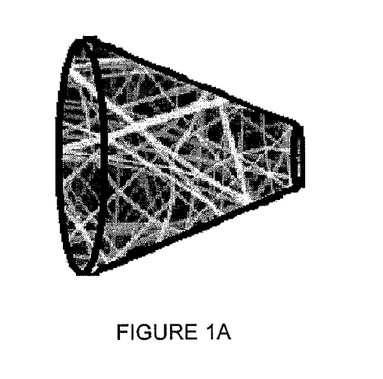
FIG. 1A depicts a 3-D cone shaped pre-concentrator comprised of a 3-D net of electrospun nano-fibers enclosed in a supporting base.
Figure 1B:
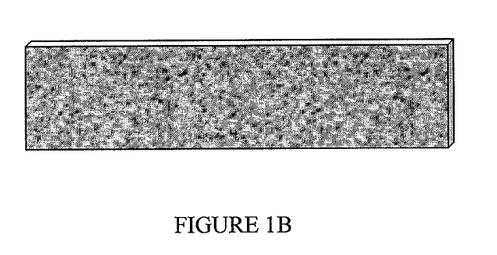
FIG. 1B depicts a rectangular prism shaped pre-concentrator.
Figure 1C:
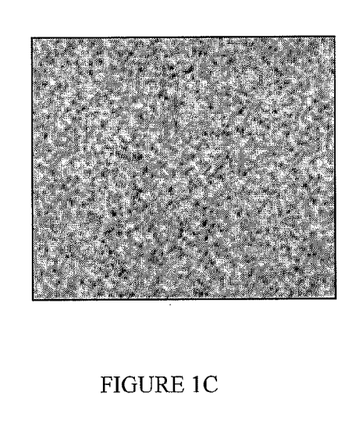
FIG. 1C depicts a rectangular 3-D sheet/filter shaped pre-concentrator, with or without a supporting base, according to a specific example embodiment of the disclosure.

FIG. 1 illustrates a variety of 3-D shapes and designs of pre-concentrators of the disclosure that comprise electrospun nano-fibers. Exemplary pre-concentrator shapes illustrated in FIGS. 1A, 1B and 1C include a 3-D cone shaped pre-concentrator made of a net of electrospun nano-fibers that may for example capture vapor flow (FIG. 1A); a 3-D rectangular prism shape that may be configured for use with a wand style detectors (or point detectors) (FIG. 1B); and a rectangular or cuboid 3-D filter shaped pre-concentrator that may for example be installed like a filter in a HVAC system. The examples and uses set forth are not limiting embodiments and a wide variety of other shapes may be generated for a wide range of uses according to the teachings of the present disclosure.

Accordingly, pre-concentrators may also be formed having 3-D designs and shapes that include but are not limited to spherical, 3-D oval, cylindrical, cubical, cuboid, square based pyramid triangular based pyramid, triangular prism, hexagonal prism, icosahedral, and/or disc shaped structures. Since compounds of interest may be present in air or water (i.e., gas or liquid medium), electrospun fibers may be assembled into pre-concentrators having 3-D structures with large surface areas for capture and concentration of such compounds.

Pre-concentrator structures may be comprised of nanofiber mats or nanofiber nets that may be further organized into complex 3-D structures. Pre-concentrators of the disclosure may or may not be enclosed in a base shape such as a housing or a support structure. A detailed discussion on generating 3-D shapes and structures of the pre-concentrators is provided later in this specification.

Figure 2:
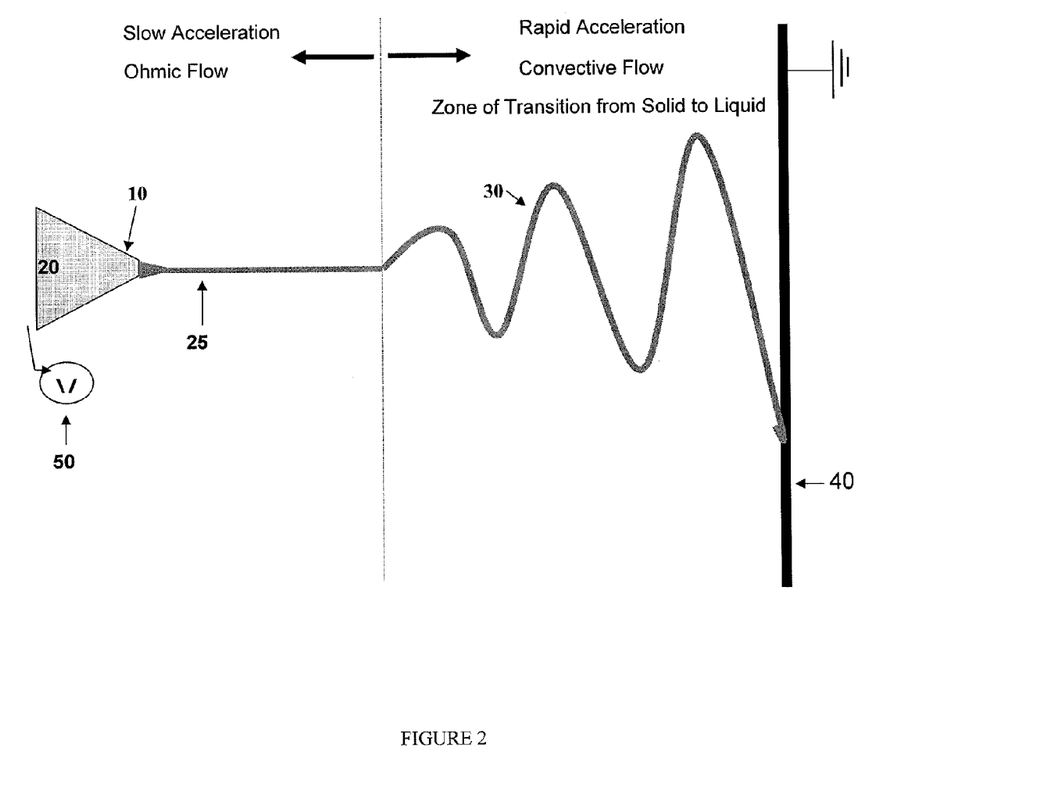
FIG. 2 illustrates an example electrospinning technique that may be used to generate electrospun nano-fibers, according to a specific example embodiment of the disclosure.

Electrospinning may be used to fabricate pre-concentrators according to certain embodiments. FIG. 2 illustrates a schematic of an electrospinning process according to certain embodiments and depicts a pipette tip 10 containing a polymer solution 20, a polymer jet 25, spinning and accumulating fibers 30, an electrospun fiber collector or target 40, and a voltage generating device 50 that can hold the pipette tip at a positive or negative potential.

Electrospinning is a straightforward and low cost electrostatic self-assembly process that generates a large variety of long polymer fibers with diameters of approximately 40 nm to about 2 µm. Electrospinning techniques have been described since the 1930's. Electrospinning comprises generating a high voltage electric field between an oppositely charged polymer fluid contained in a glass pipette and a metallic collection screen. As the voltage is increased, the charged polymer solution is attracted to the screen. Once the voltage reaches a critical value, the charge overcomes the surface tension of the suspended polymer cone formed on the tip of the glass pipette and a jet of ultrafine fibers is produced. As the charged fibers are spun, the solvent quickly evaporates and the fibers accumulate randomly on the surface of the electrospun fiber collection screen also referred to as a target. This results in a non-woven mesh of nano to micron scale fibers which have high surface areas. The charge density, polymer solution concentration and the duration of electrospinning may be varied to control fiber diameter and mesh thickness.

A pre-concentrator of the disclosure may be synthesized with electrospun fibers having a diameter average of less that about 1 micron (1µ). Accordingly, a pre-concentrator of the disclosure may be comprised of electrospun nano-fibers. Exemplary electrospun nano-fibers comprising a pre-concentrator of the disclosure may have diameters ranging from, about 1 nm to about 999 nm. This may include nano-fibers with a diameter of about 10 nm to about 100 nm, 100 nm to about 150 nm, about 150 nm to about 200 nm, about 250 nm to about 300 nm, about 300 nm to about 350 nm, about 350 nm to about 400 nm, about 400 nm to about 450 nm, about 450 nm to about 500 nm, about 500 nm to about 550 nm, about 550 nm to about 600 nm, about 600 nm to about 650 nm, about 650 nm to about 700 nm, about 700 nm to about 750 nm, about 750 nm to about 800 nm, about 800 nm to about 900 nm and about 900 nm to about 999 nm.

A variety of polymers may be used to synthesize the electrospun nano-fibers comprising a pre-concentrator of the disclosure. Some non-limiting examples include polyphenylenevinylene, polyacetylene, polythiophene, polypyrrole, polyaniline, polyphenylene sulfide, and combinations and/or derivatives thereof.

Other polymeric materials that may be used may include nylon, fluoropolymers, polyolefins, polyimides, polyesters, acrylics, rubbers, vinyls, urethanes, silicones, natural polymers of proteins, carbohydrates and DNA, and any other suitable engineering polymers or textile forming polymers. Such polymeric materials include for example acrylonitrile/butadiene copolymer, cellulose, cellulose acetate, chitosan, collagen, DNA, protein, fibrinogen, fibronectin, nylon, poly(acrylic acid), poly(chloro styrene), poly(dimethyl siloxane), poly(ether imide), poly(ether sulfone), poly(ethyl acrylate), poly(ethyl vinyl acetate), poly(ethyl-co-vinyl acetate), poly(ethylene oxide), poly(ethylene terephthalate), poly(lactic acid-co-glycolic acid), poly(methacrylic acid) salt, poly(methyl methacrylate), poly(methyl styrene), poly(styrene sulfonic acid) salt, poly(styrene sulfonyl fluoride), poly(styrene-co-acrylonitrile), poly(styrene-co-butadiene), poly(styrene-co-divinyl benzene), poly(vinyl acetate), poly(vinyl alcohol), poly(vinyl chloride), poly(vinylidene fluoride), polyacrylamide, acrylonitrile divinylbenzene copolymers, polyacrylonitrile, acrylic ester polymers, poly(divinylbenzene/ethylene glycol dimethacrylate), polydivinylbenzene/polyethyleneimine, polyamide, polyaniline, polybenzimidazole, polycaprolactone, polycarbonate, poly(dimethylsiloxane-co-polyethyleneoxide), poly(etheretherketone), polyethylene, polyethyleneimine, polyimide, polyisoprene, polylactide, polypropylene, polystyrene, polysulfone, polyurethane, poly(vinylpyrrolidone), proteins, SEBS copolymer, silk, styrene/isoprene copolymer, divinylbenzene/vinyl pyrollidinone copolymer, divinylbenzene/vinyl pyridine copolymer, poly(ethylene glycol dimethacrylate), ethylvinylbenzene-divinylbenzene copolymer, poly(vinylpyrolidone), poly(vinylpyridine), poly(diphenylphenylene oxide), Teflon polymers, chlorofluorocarbon resins, fluorocarbon resins, and others.

In some embodiments, polymer blends comprising two or more polymers that may be soluble in a common solvent, may be used, such as but not limited to poly(vinylidene fluoride)-blend-poly(methyl methacrylate), polystyrene-blend-poly(vinylmethylether), poly(methyl methacrylate)-blend-poly(ethyleneoxide), poly(hydroxypropyl methacrylate)-blend-poly(vinylpyrrolidone), poly(hydroxybutyrate)-blend-poly(ethylene oxide), protein-blend-polyethyleneoxide, polylactide-blend-polyvinylpyrrolidone, polystyrene-blend-polyester, polyester-blend-poly(hyroxyethyl methacrylate), poly(ethylene oxide)-blend poly(methyl methacrylate), poly(hydroxystyrene)-blend-poly(ethylene oxide).

In some embodiments, physical mixtures of different polymers may be used. In some embodiments, chemically linked polymers may be used.

Chemo-selectivity or bio-selectivity of a pre-concentrator of the disclosure may be conferred by 1) the nature of the polymer(s) comprising an electrospun nano-fiber including side groups on the polymer(s); and/or attached chemical/biological functional groups on the polymers; and/or derivatives of the polymer; and/or by 2) adding one or more chemical functional groups or bio-specific moieties operable to bind specifically to chemicals/biological compounds of interest, onto nano-fibers by chemical reactions or dip-coating methods; and/or by 3) functionalizing the entire 3-D nano-fiber pre-concentrator by one or more of the methods set forth here.

For example, a polymer used to form a pre-concentrator of the disclosure, may have one or more chemo-specific functional groups or biological moieties or bio-specific functional groups that may confer selective binding to one or more chemical or biological agents of interest. In other examples, a polymer may be derivatized or functionalized by chemical reactions with one or more chemical groups or biological moieties that confer chemo/bio-selective binding properties.

In some embodiments, electrospun nano-fibers comprising a pre-concentrator or a formed 3-D pre-concentrator structure may be clad via a dip coat, such as a vapor deposit with a desired chemical functional group. Multiple dip coatings may be performed to add on additional chemical functional groups. A chemical reaction may also be performed to transfer a desired functional group onto a nano-fiber. In some embodiments a functionalized silicone coating may be coated onto a nano-fiber of a pre-concentrator.

Dip-coating may be also used to create a multi-layer system, wherein an inner layer may have a dip coating of a metal (conducting agent), and additional dip coatings of functionalized silicone and/or other functional groups.

An exemplary method may involve electrospinning a polymer, e.g., a polyaniline polymer, onto a metallic net having a respective shape to obtain a 3-D nano-fiber structure of the respective shape. The 3-D nano-fiber structure may then be dipped into a bath containing a metal salt, e.g., a silver salt, which is deposited on the surface of the nano-fibers. The 3-D nano-fiber net clad with the metal e.g., silver, may then be dipped into a functionalized silicone coating, e.g., a fluorinated alcohol functionalized silicone coating, to obtain a pre-concentrator according to the disclosure.

Figure 3A:
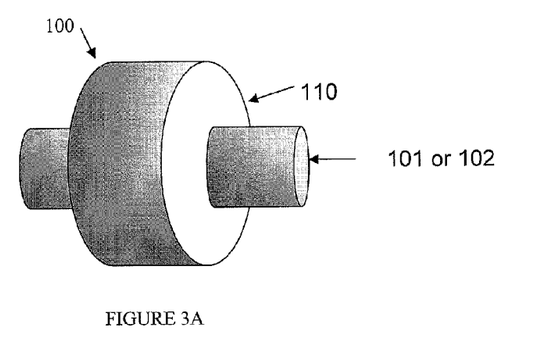
FIG. 3A illustrates a nanofiber with a conducting agent (a dopant or a metal) and a chemically functionalized coating.
Figure 3B:
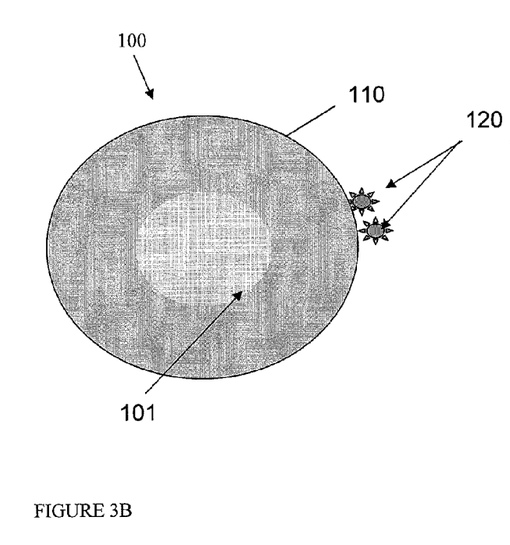
FIG. 3B illustrates a cross-sectional view of an electrospun nano-fiber having a conductive doped polymers fiber and a layer of chemical functionalized groups attracting compounds of interest.
Figure 3C:
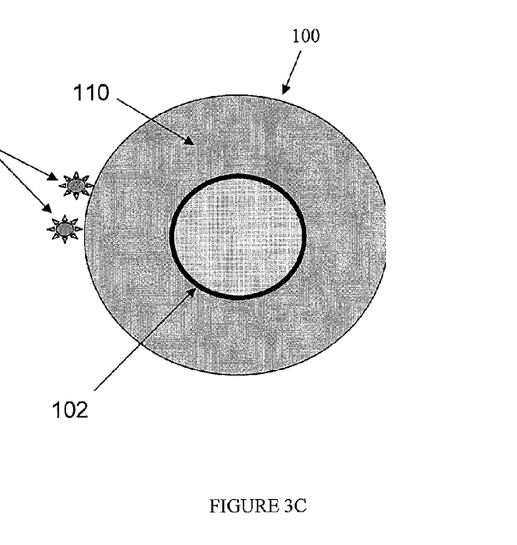
FIG. 3C illustrates a cross-sectional view of an electrospun nano-fiber having a conductive metal layer on a polymer fiber and a layer of chemical functionalized groups attracting compounds of interest, according to a specific example embodiment of the disclosure.

FIGS. 3A, 3B and 3C illustrate a schematic of an example electrospun nano-fiber structure forming a pre-concentrator of the disclosure. FIG. 3A illustrates a nano-fiber 100 with a conductive doped polymer 101 or a polymer with a metallic dip coating 102 (i.e., polymer nano-fiber with a conducting agent being a dopant or a metal) and a chemically functionalized silicone coating 110. FIG. 3B illustrates a cross-sectional view of an electrospun nano-fiber having a core of conductive doped polymer 101 surrounded by a functionalized silicone layer 110, comprising chemo-specific functionalized groups 110, attract and bind to compounds of interest 120. FIG. 3C illustrates a cross-sectional view of an electrospun nano-fiber having a conductive metal layer core 102 (formed by dip coating) surrounding which is a layer of functionalized silicone 110, attracting compounds of interest 102.

A dip coating method may be performed using a dissolved metal salt or a dissolved polymer coating (functional group), dissolved either in water or a solvent to form a solution of metal salt or a solution of polymer coating (e.g., functionalized silicone). A 3-D pre-concentrator net may be then dipped into the metal salt solution and/or polymer coating solution under conditions that allow the dissolved substance in the respective solution to accumulate on the pre-concentrator net. Exemplary conditions for allowing deposition of metal or functionalized silicone/polymer coating may include but are not limited to incubation for a certain time, mixing or stirring while incubation and/or incubating at a certain temperature.

Exemplary methods for chemical reactions with functionalized silicone coating for adding functional groups onto a 3-D net pre-concentrator may be described in the example below. A polyaniline polymer may be electrospun on to a metal 3-D structure. The 3-D polymer structure may then be subject to protonation using for example, a protonating acid such as hydrochloric acid or sulfuric acid. A metal such as silver may then be deposited on the surface of the 3-D net pre-concentrator by dip coating by dipping into a solution of silver nitrate. After the silver is fully deposited, the composite may be dipped into an organic solution containing a vinylmethylsiloxane homopolymer. The polymer is then allowed to dry on the surface of the pre-concentrator fibers. The siloxane may then be reacted with hexafluoroacetone gas under inert conditions.

Chemo-selective functional groups or functionalities may be deposited by chemical vapor deposition (CVD) onto the surface of an electrospun fiber on a mat or a 3-D structure. Such processes referred to as initiated CVD (iCVD) may be accomplished by thermal or plasma activated processes. Chemo-selective functionalities added by these methods may form a tethered part of a polymer chain once deposited. iCVD may be generally carried out in a reactor chamber under a mild vacuum into which a mixture of precursor gases (e.g., glycidyl methacrylate (GMA), octamethylcyclotetrasiloxane (D4) or hexafluoropropylineoxide (HPFO)), may be injected. A substrate (such as a nano-fiber mat or a nano-fiber 3-D structure) may be placed underneath an array of filament wires that are raised sufficiently to ensure that the substrate is at or near room temperature. Precursor gases decompose and form polymer radicals or monomers as they pass through the filament array and condense onto the substrate, where they grow and form into a polymer film. This process result is a conformal coating of polymer film containing the chemo-selective moieties on the nano-fiber (of a pre-concentrator) that may range in thickness from the Angstrom range to microns.

In some embodiments, pre-concentrators of the disclosure may be synthesized with a doped conducting polymer system. For example, dopants may be incorporated into the polymer or electrospun nano-fiber by physically mixing a dopant with the polymer solution while generating the nano-fiber.

In some embodiments, metal conducting agents may be coated onto electrospun nano-fibers as set forth above. A dopant or a metal (i.e., a conducting agent) may confer the property of resistive heating to a pre-concentrator of the disclosure. For example, when an electrical current is passed through a doped and/or metal coated electrospun fiber, a Joule heating effect at the nano-scale level may be generated allowing dissociation of weak non-covalent forces by which a compound of interest may be bound to the electrospun fiber in a pre-concentrator of the disclosure. Accordingly, in some embodiments, compounds of interest that are bound to a pre-concentrator of the disclosure by means such as adsorption, hydrogen bonding, or dipole-dipole attraction may be released upon being subject to an electric current, radiant sources or any other form of heat that can cause a nano-scale heating effect on a nano-fiber.

In some embodiments, electrospun fiber pre-concentrators of the disclosure comprising a conductor may be very efficient at releasing a bound compound of interest (for subsequent detection by a detector means) due to the uniform nano-scale heating effects. A uniform and/or a substantially simultaneous release of analytes of interest from the entire electrospun fiber pre-concentrator 3-D structure may result thereby releasing sufficient concentration of the analytes/compound of interest for detection by a detector.

Since some analytes, e.g., chemicals contained in explosives, are present at very low concentrations, unless a pre-concentrator can release sufficient concentration of such an analyte, it may not be detectable by a detector. Semiconducting properties of the electrospun fibers of the disclosure may result in highly sensitive and rapid detection of a compound of interest.

In some embodiments, electrospun nano-fibers comprised in pre-concentrators and/or devices and/or systems of the disclosure, have an intrinsic heater. An intrinsic heater provides an advantage over a dependence on contact with an external heater for heating of an electrospun nano-fiber. For example, an intrinsic heater may result in uniform and substantially simultaneous heating across nano-fibers of a 3-D structure and may cause a substantially simultaneous release of analytes of interest that may be bound to the pre-concentrator.

In another aspect, desorption of a compound of interest from a pre-concentrator of the disclosure may include passing a desorbing gas or liquid, i.e., desorbing medium, through the nanofiber net structure. The desorbing medium comprises a gas or a liquid that has a higher affinity for the analyte than the chemo-selective nanofiber structure.

Methods for Generating a Pre-Concentrator

In some embodiments the present disclosure provides methods for generating a pre-concentrator comprising 3-D nano-fiber structures. Such a method may comprise providing a mold having a desired 3-D structure and electrospinning nano-fibers directly into the mold to obtain a pre-concentrator. The 3-D mold of a respective shape may function as a nano-fiber collector of an electrospinning apparatus.

In some embodiments of such a method, the mold may be removable or dissolvable. Accordingly, a method may also comprise a step of removing or dissolving the mold. In such embodiments, the 3-D structure of a pre-concentrator may be a self supporting shape.

In some embodiments the mold may be retained as a casing surrounding the 3-D electrospun fiber pre-concentrator. In some embodiments, molds that may be retained be made of a conducting material such as a metal. Retained molds may function as housings or support structures and provide mechanical support; and/or as and/or may provide electrical connectivity to a voltage source; and/or may function as conductors of electricity, heat or cold.

In one embodiment, a method to form a pre-concentrator may further comprise dip-coating a metal conducting agent onto the 3-D nano-fiber structure; and functionalizing the nano-fibers with appropriate chemical groups and/or adding a functionalized silicone coating.

Yet another method for generating a 3-D pre-concentrator may comprise providing a 3-D mold of a respective shape; incorporating a dopant as a conducting agent into the polymer; electrospinning the dopant incorporated polymer into the 3-D mold to form a 3-D nano-fiber structure; and incorporating chemical functional groups into the fibers by dip coating and/or functionalized silicone methods.

A nano-fiber collector or mold may be a 3-D shaped structure having shapes such as, but not limited to, a cylindrical structure, a cone-shaped structure, a rectangular prism, a sphere, a cube, or a concentric ring, into which fibers may be spun. The shape of a 3-D net may be optimized to allow maximum air/liquid flow contact with the adsorbing polymers that comprise the electrospun fibers of the net.

In other embodiments, a method to generate a 3-D structure of an electrospun fiber may comprise spinning a mat of electrospun fibers; bending or shaping the mat into a desired shape. The mat may also be alternatively placed in a mold or shaped structure to give it a desired 3-D shape.

In some embodiments, the design and shape of the 3-D net shaped pre-concentrator may be optimized to provide maximum capture of ambient gas and/or air and/or liquid flow, and to allow flexible positioning with respect to a device/system (such as a sampling or detecting device/system) or a means that houses a pre-concentrator. Furthermore, the design and shape of the 3-D net shaped pre-concentrator may be optimized to cooperate with one or more external detector means and/or devices for optimal capture of desorbed analytes during detection. For example, a concentric ring shaped 3-D structure of electrospun nanofibers may be assembled as a pre-concentrator and detector may be placed in the center of such a pre-concentrator.

The high surface area-to-volume ratio of the electrospun fibers of the disclosure in combination with the 3D pre-concentrator net design may allow for simpler polymer chemistries to be used for rendering the polymers and/or fibers chemo-selective or bio-selective.

Pre-Concentrator Devices and Systems

Pre-concentrators of the disclosure may be adapted for use in a variety of sampling devices and/or detection devices. In some embodiments, a sampling device may comprise a pre-concentrator and an air/liquid flow means or device that is configured to flow or pass air/liquid from the environment or surroundings through the pre-concentrator, thereby enabling the binding of any chemical/biological agent of interest to the chemo-selective or bio-selective moieties onto the chemo-selective or bio-selective moieties of a pre-concentrator nanofiber. Non-limiting exemplary air flow means or devices include air pumps, fans and other air circulation devices and may further include components such as power generating devices or batteries. The components of a sampling device of the disclosure may be housed in one or multiple housings that may be connected to each other.

One or more compounds of interest, that may be bound and concentrated by a pre-concentrator according to the disclosure, may be subsequently or simultaneously released and detected by a suitable detector means. Use of electrospun nano-fibers as pre-concentrators, with a separate detector for detection of bound analytes, reduces detection of false positives that may otherwise be detected if the detection system and/or method relied on detecting changes to nanofiber characteristics (such as optical fluorescence, resistivity or impedance) as these changes may occur in a nanofiber irrespective of which analyte is bound. Accordingly, in some embodiments, a detecting device of the disclosure may comprise a pre-concentrator and a suitable detector.

A system or a device of the disclosure may comprise devices for binding, concentrating, releasing and/or detecting compounds of interest. A detecting device may also comprise a sampling device such as an air/liquid flow device.

A detector may comprise one or more devices configured to detect various compounds of interest and may include, but are not limited to, a chemical detector, a biological detector, an explosives detector, and a radiological detector. In some embodiments, a detector may be operable to determine the biological species, chemical species, class of the chemical species, or class of the biological species of the compound of interest.

Non-limiting examples of detectors operable to identify chemical species or classes of chemicals that a compound of interest may belong to include spectrometers used for mass spectroscopy (MS), Raman spectroscopy, laser-induced breakdown spectroscopy (LIBS), Fourier Transform Infrared Spectroscopy (FTIR), SAW detection, optical sensors, chromatography methods, and combinations thereof. Radioactive agents may be detected by radioactivity detectors that may comprise Geiger counters, and/or scintillators.

In some embodiments, where detecting comprises identifying a biological agent, a detecting method may comprise immunological methods (using for example fluorescent detection), biochemical methods, and/or nucleic acid detection methods to identify a biological pathogen or a biological toxin.

In some embodiments, a pre-concentrator of the disclosure may be applied to a commercial off the shelf (COTS) sensor/detector to enhance its sensitivity. Electro-spun pre-concentrators may be used in concert with a number of commercial chemical or biological sensors (COTS) to increase their sensitivity or to decrease their false alarm rate. For example, electronic nose-like devices may be used, sensors based on colorimetric sensor arrays may be used, and/or sensors used in medical breathalyzer's may be adapted to detect other volatile organic compounds with high accuracy in conjunction with the pre-concentrators of the disclosure.

The electro-spun pre-concentrator's (EPC) of the disclosure may be integrated with one or more of the COTS sensors. For example, an EPC may be a backplane in a colorimetric sensor array system. Alternatively, an EPC may be co-axial with each sensor element in a colorimetric array.

Figure 4A:
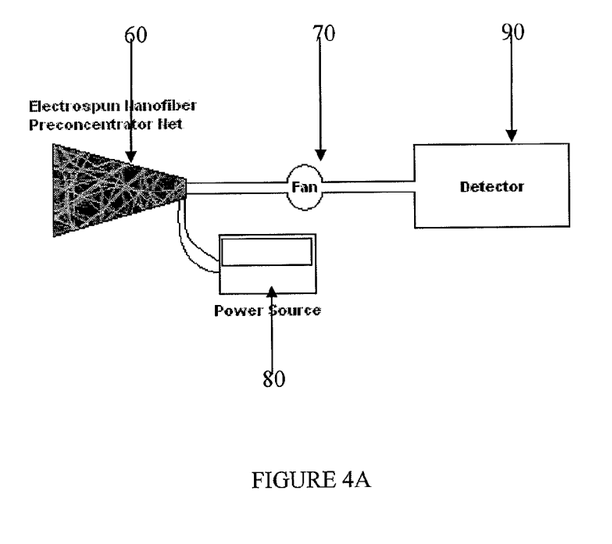
FIG. 4A depicts a pre-concentrator device comprising a conical 3D-net structure of electrospun nano-fibers, an air-flow device (fan), a power supply and a detector, according to a specific example embodiment of the disclosure.
Figure 4B:
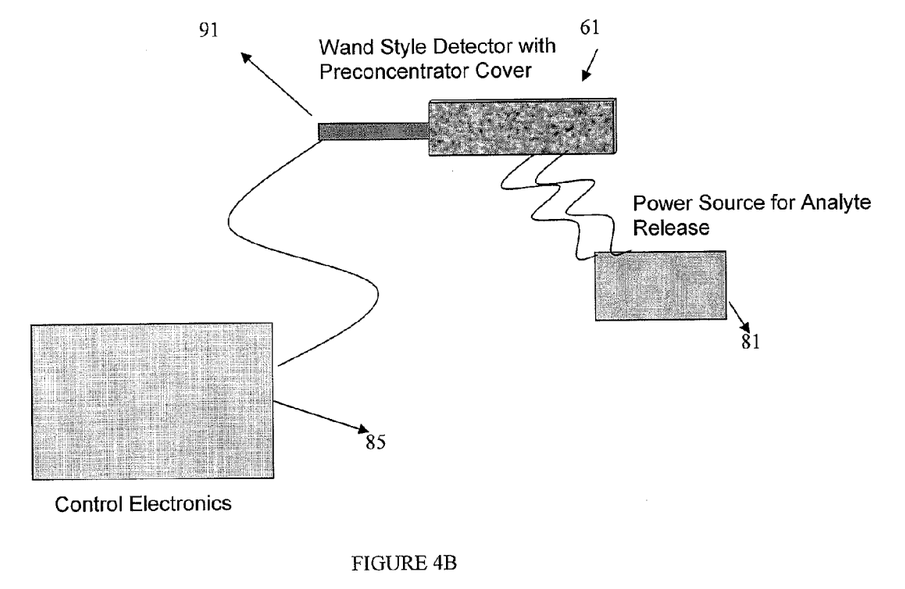
FIG. 4B depicts a pre-concentrator device and detection system comprising a rectangular pre-concentrator 3D-net structure disposed in a wand style detector, control electronics and a power source, according to a specific example embodiment of the disclosure.
Figure 4C:
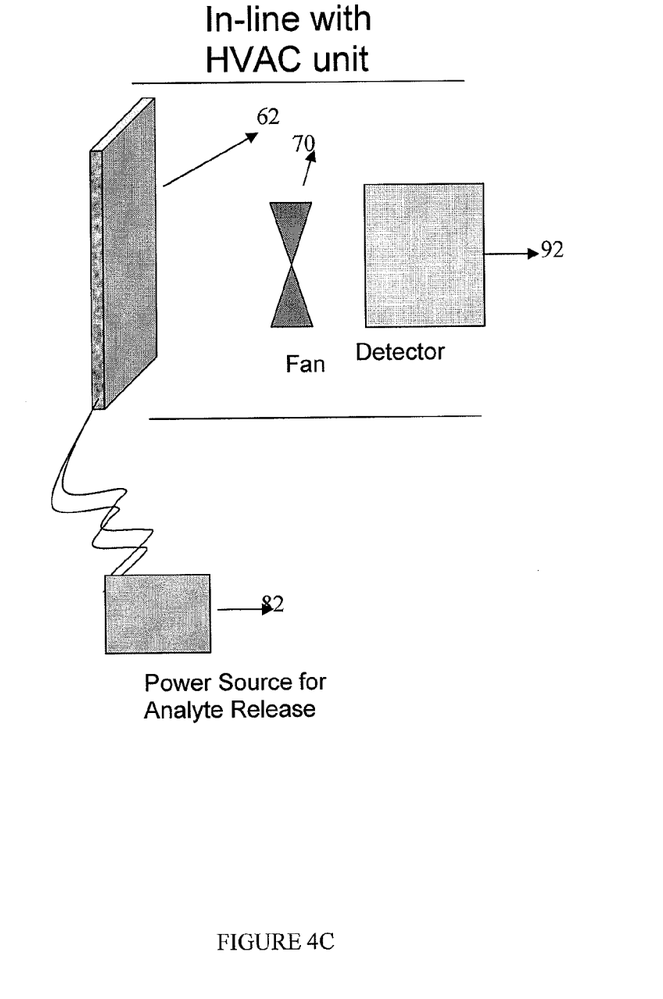
FIG. 4C illustrates a pre-concentrator device and detection system comprising a pre-concentrator having a rectangular filter made of a 3D-net of electrospun nano-fibers, an air-flow device (fan), a detector and a power source, incorporated into a HVAC type of system, according to a specific example embodiment of the disclosure.

FIGS. 4A, 4B and 4C depict example detector devices and systems comprising a pre-concentrator 3-D net of the disclosure wherein a pre-concentrator may operate in concert with a detector. FIG. 4A depicts a pre-concentrator 60 and a fan or an air pump 70 that may be used to mechanically pump air through the pre-concentrator enabling a more efficient capture of agents of interest in the air sample (i.e., a sampling device). In alternate embodiments, an air flow-over design may be used (not expressly depicted). A power source 80 may activate the sampling device and begin the sampling system. This pre-concentrator device may be also referred to as a sampling device or sampling system. Any detector 90 or sensing system, including those described above, may be used in conjunction with a sampling system as shown in FIG. 4A, to obtain a detector device/system. In such devices, power source 80 may also facilitate passing an electrical current through the pre-concentrator fibers for release of agents of interest to the detector 90. Power source 80 may also be a source of radiant energy such as laser beams or uv light.

FIG. 4B depicts a rectangular prism shaped pre-concentrator 61 coupled to a wand-style detector 91. Control electronics 85 may be used to control the detector and the release and analysis of captured analyte from the pre-concentrator by the detector.

Yet another example pre-concentrator system is depicted in FIG. 4C which shows a rectangular filter shaped 3-D pre-concentrator 62 connected to a power source 82 that may provide power for inducing analyte release, a fan or air-flow device 70 and detector 92 which are operably linked to each other and may function in-line with an HVAC unit.

In some embodiments, pre-concentrators, housed in suitable housing means and/or combined with an air sampling device, may be used alone to first concentrate a sample and may be later operably attached to a suitable detector/sensor device for release and detection of the contents of the sample. In other embodiments, a pre-concentrator and/or a sampling device may be used in conjunction with a detector for substantially simultaneous release and detection of a bound sample. In light of this disclosure, other combinations of various pre-concentrator geometries and detectors may also be used.

In some embodiments, a sampling device or a detector device comprising a pre-concentrator of the disclosure may be further combined with other components, equipment or devices, such as but not limited to, output analyzers, signal detectors, power devices, computers, and/or printers, to form a sampling system and/or a detection system. In some embodiments, a system of the disclosure may be operable to concentrate, detect, analyze and/or generate data that may be easily interpreted, (for e.g., by an operator or a computer). Such systems may further comprise an alarm component that may be configured to raise an alarm if harmful compounds such as chemical/biological warfare agents, radioactive materials, explosives, toxic industrial chemicals, or pollutants are detected.

A detection device and/or system of the disclosure may improve the sensitivity of the detection limits of different compounds of interests (analytes). Since the minimal concentration range required for the detection of different chemical and biological agents of interest may vary by more than $10^6$, the sample collection time of a pre-concentrator device of the disclosure (e.g. sampling device/system), may be varied. Collection of sample over a longer timeframe allows for binding and concentration of higher concentration of analytes, thereby producing a higher confidence in detection. In some embodiments, multiple pre-concentrator's may be used, each pre-concentrator having specificity for one compound of interest. Multiple pre-concentrator's may then be operably connected to a detector means that is operable to detect multiple samples.

Detection devices and/or systems of the disclosure may be tailored to concentrate one or more specific chemical or biological analytes based on one or more chemo-selective functional groups on a pre-concentrator (i.e., chemo-selective polymers or chemo-selective functional groups added onto an electrospun fibers) or on one or more bio-selective moiety on a pre-concentrator (i.e., a molecule a chemical or a biological compound that can recognize and bind to a biological compound of interest added on to an electrospun fiber). Chemo-selective and/or bio-selective pre-concentration provides several advantages over physical techniques used historically, including specificity and lesser false positives.

The detection devices of the disclosure may be operable to selectively release (e.g., desorb) a bound compound, for controlled sampling and reduction of false positives. The presence of a separate detector (or detector system) allows for obtaining secondary information on any compounds that may be bound in addition to compounds of interest thereby reducing false positives. Secondary information may be obtained by analysis of empirical data such as temperature of release, rate of release, and/or changes in voltage at release.

Devices and systems of the disclosure may be incorporated into existing facilities for detecting chemicals, or screening systems such as those installed in public places, airports, doorways of buildings, baggage scanners, scanners for detection of industrial waste, or environmental pollution detectors. In such devices and systems, a pre-concentrator of the disclosure may be configured to be reusable, disposable and/or replaceable.

Methods of Use

In some embodiments, the disclosure relates to methods for concentrating at least one chemical or biological compound from the environment (such as air, water) and may comprise providing a 3-D structure comprising electrospun nanofibers that comprise a conducting agent such as a metal and/or a dopant; and at least one chemo-selective functional group or bio-selective moiety operable to releasably bind to at least one chemical or biological compound and allowing a sample (of air or water) containing (or suspected of containing) the chemical or biological compounds to make contact with the electrospun nanofiber 3-D structure. This may be achieved for example by an air flow device pumping air samples into the 3-D electrospun nanofiber structure or a water pump pumping water or liquid samples into the 3-D structure. Contact of a chemical or biological compound in the sample having specificity for a chemo-functional group on the electrospun fibers results in binding and concentrating the chemical or biological compounds on the electrospun fibers. Binding may be achieved by weak non-covalent bonds or adsorption.

The disclosure also describes methods for detecting chemical or biological compounds that may be bound or concentrated by a pre-concentrator. Such a method may comprise, in addition to the steps above, detecting one or more chemical or biological compound that is bound and may comprise detaching the bound chemical or biological compounds from the electrospun fibers (e.g., by generating conditions that cause release of bound compounds, i.e., conditions (e.g., heating, resistive heating) that may cause desorption, or breaking of weak non-covalent bonds), and determining the biological species, chemical species, class of the chemical species, class of the biological species, or radioactivity, of the detached compound.

While the methods, compositions, devices and systems of the disclosure are configured to bind, concentrate and detect any chemical or biological moiety, CBRNE agents that may be used for warfare and/or terrorist activities are of particular interest. Industrial pollutants and environmental pollutants are other agents of interest.

Exemplary chemicals that may be concentrated and detected by the methods, compositions, devices and systems, of the disclosure include chemical warfare agents, toxic chemicals and pollutants, such as but not limited to, Tabun, Sarin, Soman, VX, mustard, lewisite, phosgene, chlorine, ammonia, cyanide, Mace®, pepper spray, nerve agents, vesicants, industrial chemicals, and riot control agents.

Exemplary biological agents that may be concentrated and detected by the methods, compositions, devices and systems of the disclosure include but are not limited to, harmful bacteria, bacterial spores, viruses, fungi, bacterial and fungal toxins, cytotoxins, neurotoxins, including genetic variants thereof that may be more virulent, harder to treat, or more toxic. Some non-limiting examples of bacteria that may be used in biological warfare include *Bacillus anthracis, Yersinia pestis, Francisella tularensis, Vibrio cholerae, Clostridium botulinum, Chlamydia psittaci, Shigella dysenteriae, Staphylococcus aureus, Burkholderia mallei,* and *Salmonella typhi,* that may cause diseases such as anthrax, plague, tularemia, cholera, typhoid, and Q-fever. Exemplary viruses may include, Variola virus, Venezuelan equine encephalitis virus, dengue virus, hantavirus, Marburg virus, Ebola virus, Crimean Congo hemorrhagic fever virus, and arena viruses. Non-limiting bio-selective moieties toward these biological agents may include antibodies, antigens, including hybrid or fusion proteins, to one or more of these agents or any peptides, proteins, glycopeptides, or nucleic acids that may recognize and bind to one or more of these agents.

Examples of explosive agents that may be concentrated and detected by the methods, compositions, devices and systems of the disclosure include but are not limited to, ANFO, amatol, ammonium nitrate, ammonium picrate, dynamite, guanidine nitrate, gunpowder, HMX, hexanitrostilbene, lead azide, lead styphnate, mannitol hexanitrate, mercury fulminate, naphthacene, nitroglycerine, nitroguanidine, PBX explosive, pentaerythritol, tetranitrate, picric acid, RDX, TATP, TNT, triaminotrinitrobenzene, tritonal.

Exemplary radioactive materials that may be components of nuclear weapons include Uranium-235 ($U^{235}$) and/or Plutonium-239 ($Pu^{239}$) both of which may facilitate an explosion or an explosive chain reactions and may releases lethal radioactivity.

As will be understood by those skilled in the art who have the benefit of the instant disclosure, other equivalent or alternative compositions, devices, methods, and systems for pre-concentrating and detecting chemical/biological agents of interest may be envisioned without departing from the description contained herein. Accordingly, the manner of carrying out the disclosure as shown and described is to be construed as illustrative only.

Persons skilled in the art may make various changes in the shape, size, number, and/or arrangement of parts without departing from the scope of the instant disclosure. For example, a pre-concentrator may have a 3D configuration of any shape or size, may be assembled from multiple nano-fiber mats, nano-fiber filters or nano-fiber nets and may have one or more pre-concentrator units (with different chemo-selective groups) for the detection of multiple analytes of interest as described herein. In addition, the size and shape of an electrospun fiber 3-D structure may be adapted, scaled up or down to fit into any existing sampling, detection and/or screening device that is in use at for example public places where for example CBRNE threats may be possible or where pollutants and toxic agents may be found. A pre-concentrator nano-fiber may be configured and arranged to be reusable, disposable, serviceable, interchangeable, and/or replaceable.

A device or system for pre-concentrating and/or sampling, in accordance with the disclosure, may or may not comprise, in some embodiments, an attached detector. In such embodiments, detection may be carried out later with separate detectors.

Where ranges have been provided, the disclosed endpoints may be treated as exact and/or approximations as desired or demanded by the particular embodiment. In addition, it may be desirable in some embodiments to mix and match range endpoints. In some embodiments, the term "about" when applied to a numeric value may refer to that numeric value plus or minus about 1% of that value, plus or minus about 5% of that value, plus or minus about 10% of that value, plus or minus about 25% of that value, and/or plus or minus about 50% of that value. When the numeric value is provided as an endpoint to a range, the term "about" may have more or less flexibility depending on the extent of the range, according to some embodiments. For example, if the range covers a single order of magnitude (e.g., from about 1 to about 10), "about" may have less flexibility (e.g., expanding endpoints by ±5%). For a range that covers several orders of magnitude (e.g., from about 0.1 to about 100), however, the endpoints may have more flexibility (e.g., expanding endpoints by ±50%). In some embodiments, a concentration range that includes the term "up to" (e.g., up to 1 mM of NaCl) may include a lower endpoint that include any amount of the material above zero (e.g., any detectable trace of NaCl). The term "up to," in some embodiments, may contemplate and/or require that some non-zero amount of the specified material is present.

These equivalents and alternatives along with obvious changes and modifications are intended to be included within the scope of the present disclosure. The present disclosure is intended to be illustrative, but not limiting, of the scope of the disclosure. The appended claims are similarly intended to be illustrative, but not limiting, of the scope of the disclosure.

What is claimed is:

1. A pre-concentrator comprising:
   electrospun nanofibers comprising:
   at least one polymer;
   at least one chemo-specific functional group or bio-specific moiety configured to selectively and releasably bind to and concentrate one or more compounds;
   at least one conducting agent; and an intrinsic heater configured to heat the electrospun nanofibers without dependence on contact with an external heater to release the one or more releasably bound compounds;

wherein the electrospun nanofibers are organized into a three-dimensional (3-D) structure.

2. The pre-concentrator of claim 1, wherein the at least one chemo-specific functional group or bio-specific moiety has binding properties different from release properties for the one or more compounds.

3. The pre-concentrator of claim 1, wherein the at least one chemo-specific functional group or bio-specific moiety is configured to bind to the one or more compounds by non-covalent bonds or weak mechanisms.

4. The pre-concentrator of claim 1, wherein the at least one chemo-specific functional group or bio-specific moiety is a transition metal complex, a fluorinated alcohol, or a crown ether.

5. The pre-concentrator of claim 1, wherein:
the electrospun nanofibers comprise at least two electrospun nanofiber types;
a first of the electrospun nanofiber types has at least one different chemo-specific functional group or bio-specific moiety as compared to a second of the electrospun nanofiber types; and
the electrospun nanofiber types are operable to bind to different compounds.

6. The pre-concentrator of claim 1, wherein the at least one conducting agent is a dopant.

7. The pre-concentrator of claim 6, wherein the dopant is a metal, nickel, chrome, copper, nickel alloy, tungsten, steel, carbon, or any combination or alloy thereof.

8. The pre-concentrator of claim 1, wherein the at least one conducting agent comprises at least one of: silver, copper, gold, nickel, or chromium.

9. The pre-concentrator of claim 1, wherein the electrospun nanofibers are 100 nm to 400 nm in diameter.

10. The pre-concentrator of claim 1, wherein the one or more compounds are chemical agents, biological agents, radioactive agents, nuclear agents, explosive agents, or combinations thereof.

11. The pre-concentrator of claim 1, wherein the polymer is a polyphenylenevinylene, a polyacetylene, a polythiophene, a polypyrrole, a polyaniline, a polyphenylene sulfide, a silicone, or any combination or derivative thereof.

12. The pre-concentrator of claim 1, wherein the 3-D structure comprises at least one of: nanofiber mats or nanofiber nets.

13. The pre-concentrator of claim 1, wherein the intrinsic heater is configured to heat the electrospun nanofibers by at least one of the following:
resistive heating of the electrospun nanofibers,
nanoscale Joule-heating effects,
substantially simultaneous heating,
subjecting a binding between the electrospun nanofibers and the one or more releasably bound compounds to electric current, and
subjecting the binding to a form of heat that causes a nanoscale heating effect on the electrospun nanofibers.

14. The pre-concentrator of claim 1, wherein the electrospun nanofibers are configured to release the one or more releasably bound compounds bound to the electrospun nanofibers based on at least one of:
dissociation of weak non-covalent bonds, and
selective desorption.

15. The pre-concentrator of claim 1, wherein the at least one conducting agent is configured to enable at least one of:
substantially uniform heating of the electrospun nanofibers, and
substantially uniform cooling of the electrospun nanofibers.

16. A pre-concentrator apparatus comprising:
electrospun nanofibers configured as a three-dimensional (3-D) structure, the electrospun nanofibers comprising:
at least one polymer;
at least one chemo-specific functional group or bio-specific moiety configured to selectively and releasably bind to and concentrate one or more compounds;
at least one conducting agent; and
an intrinsic heater configured to heat the electrospun nanofibers without dependence on contact with an external heater to release the one or more releasably bound compounds.

17. The pre-concentrator apparatus of claim 16, wherein the at least one conducting agent is a dopant comprising at least one of: nickel, chrome, copper, nickel alloy, tungsten, steel, or carbon.

18. The pre-concentrator apparatus of claim 16, wherein the at least one chemo-specific functional group or bin-specific moiety has binding properties different from release properties for the one or more compounds.

19. The pre-concentrator apparatus of claim 16, wherein the at least one chemo-specific functional group or bio-specific moiety is configured to bind to the one or more compounds by non-covalent bonds.

20. The pre-concentrator apparatus of claim 16, wherein:
the electrospun nanofibers comprise at least two electrospun nanofiber types;
a first of the electrospun nanofiber types has at least one different chemo-specific functional group or bio-specific moiety as compared to a second of the electrospun nanofiber types; and
the electrospun nanofiber types are operable to bind to different compounds.

21. The pre-concentrator apparatus of claim 16, wherein the one or more compounds comprise at least one of: chemical agents, biological agents, radioactive agents, nuclear agents, or explosive agents.

22. The pre-concentrator apparatus of claim 16, wherein the electrospun nanofibers are 100 nm to 400 nm in diameter.

23. The pre-concentrator apparatus of claim 16, wherein the 3-D structure comprises at least one of: nanofiber mats or nanofiber nets.

* * * * *